United States Patent [19]

Drabek

[11] 4,006,229
[45] Feb. 1, 1977

[54] INSECTICIDAL AND ACARICIDAL TRIHALOPHENYL THIOPHOSPHATES

[75] Inventor: Jozef Drabek, Basel, Switzerland
[73] Assignee: Ciba-Geigy AG, Basel, Switzerland
[22] Filed: July 21, 1975
[21] Appl. No.: 597,805

Related U.S. Application Data

[62] Division of Ser. No. 192,477, Oct. 26, 1971, Pat. No. 3,919,362.

[30] Foreign Application Priority Data

Oct. 26, 1970   Switzerland ............... 15775/70
Sept. 7, 1971   Switzerland ............... 13101/71

[52] U.S. Cl. .................. 424/225; 424/217; 424/220; 424/222
[51] Int. Cl.² .................................... A01N 9/36
[58] Field of Search .................. 424/225; 260/964

[56] References Cited

UNITED STATES PATENTS

| | | | |
|---|---|---|---|
| 2,599,375 | 6/1952 | Drake et al. | 260/964 |
| 2,761,806 | 9/1956 | Boyer | 260/964 |
| 3,444,274 | 5/1969 | Schrader | 260/964 |
| 3,663,665 | 5/1972 | Kume et al. | 260/964 |

*Primary Examiner*—V. D. Turner
*Attorney, Agent, or Firm*—Harry Falber

[57] ABSTRACT

Compounds of the formula

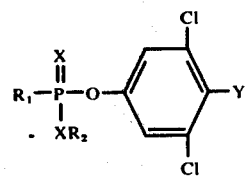

wherein $R_1$ is $C_1$–$C_4$ alkyl, $C_1$–$C_4$ alkoxy, amino, $C_1$–$C_4$ alkylamino, bis-($C_1$–$C_4$ alkyl)amino or a phenyl group unsubstituted or substituted up to three times with $C_1$–$C_4$ alkyl, $C_1$–$C_4$ alkoxy and/or halogen; $R_2$ is $C_1$–$C_4$ alkyl, X is oxygen or sulphur and Y is chlorine, bromine or iodine, their manufacture and their use for combating various pests.

4 Claims, No Drawings

INSECTICIDAL AND ACARICIDAL TRIHALOPHENYL THIOPHOSPHATES

This is a division of application Ser. No. 192,477 filed on Oct. 26, 1971, now U.S. Pat. No. 3,919,362.

This invention relates to novel phosphorus organic compounds, a process for their manufacture, their use for combating pests and pest control agents which contain them as active substance.

According to the present invention there is provided a compound of the formula

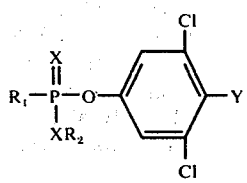

wherein $R_1$ is $C_1 - C_4$ alkyl, $C_1 - C_4$ alkoxy, amino, $C_1 - C_4$ alkylamino, bis-($C_1 - C_4$ alkyl)amino or a phenyl group unsubstituted or substituted up to 3 times with $C_1 - C_4$ alkyl, $C_1 - C_4$ alkoxy and/or halogen, $R_2$ is $C_1 - C_4$ alkyl and X is oxygen or sulphur, while Y is a chlorine, bromine or iodine atom.

The term halogen includes fluorine, chlorine, bromine and iodine.

The $C_1 - C_4$ alkyl, $C_1 - C_4$ alkoxy- groups which may be represented by $R_1$ and $R_2$ can be branched or straight chain. Examples of such groups are inter alia: methyl, methoxy, ethyl, ethoxy, propyl, propoxy, isopropyl, isopropoxy, n-, i-, sec.- and tert. butyl.

Good activity is possessed by those compounds of formula I wherein R is methyl, ethyl, n-propyl, isopropyl, or methoxy, ethoxy, isopropoxy, amino, methylamino, dimethylamino, ethylamino or diethylamino or a phenyl group unsubstituted or substituted up to 3 times with substituents selected from the group of methyl, ethyl, isopropyl, sec. butyl, methoxy, ethoxy, n-propoxy, isopropoxy chlorine, bromine and iodine, and $R_2$ is methyl, ethyl, propyl and isopropyl, X is oxygen or sulphur and Y is chlorine or bromine.

Of particular value however are those compounds of formula I wherein $R_1$ is methyl, ethyl, methoxy, ethoxy, amino, methylamino, dimethylamino or phenyl, $R_2$ is methyl or ethyl, X is oxygen or sulphur and Y is chlorine or bromine.

Examples of such compounds are inter alia:
1. methylamido-O-ethyl-O-(3,4,5-trichlorophenyl)-thiophosphate
2. phenyl-O-methyl-O-3,4,5-trichlorophenylthionophosphonate
3. phenyl-O-ethyl-O-3,4,5-trichlorophenylthionophosphonate
4. O,O-dimethyl-O-3,4,5-trichlorophenylthiophosphate
5. O,O-diethyl-O-3,4,5-trichlorophenylthiophosphate
6. phenyl-O-ethyl-O-3,4,5-trichlorophenylphosphonate
7. O-dimethyl-O-3,4,5-trichlorophenylphosphate
8. O,O-diethyl-O-3,4,5-trichlorophebylphosphate
9. phenyl-O-ethyl-O-3,5-dichloro-4-bromophenylthionophosphonate
10. phenyl-O-methyl-O-3,5-dichloro-4-bromophenylthionophosphonate
11. O,O-dimethyl-O-3,5-dichloro-4-bromophenylthionophosphate
12. O,O-diethyl-O-3,5-dichloro-4-bromophenylthionophosphonate
13. ethyl-O-ethyl-O-3,4,5-trichlorophenylthionophosphonate
14. methyl-O-methyl-O-3,4,5-trichlorophenylthionophosphonate
15. ethyl-O-ethyl-O-3,5-dichloro-4-bromophenylthionophosphonate
16. methylamino-O-methyl-O-3,5-dichloro-4-bromophenylthionophosphate
17. methylamino-O-ethyl-O-3,5-dichloro-4-bromophenylthionophosphate
18. amino-O-ethyl-3,5-dichloro-4-bromophenylthionophosphate
19. isopropylamino-O-ethyl-O-3,5-dichloro-4-bromophenylthionophosphate
20. phenyl-5-ethyl-O-3,4,5-trichlorophenylthionophosphate
21. methylamino-O-methyl-3,4,5-trichlorophenylphosphate
22. methylamino-O-ethyl-O-3,4,5-trichlorophenylphosphate
23. methylamino-S-ethyl-3,4,5-trichlorophenylphosphonate
24. O-ethyl-S-ethyl-3,4,5-trichlorophenylphosphate The compounds of formula I according to the invention are suitably obtained by methods known in principle, e.g.

a. by allowing a phenol of general formula

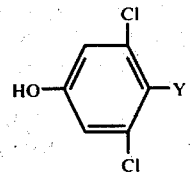

wherein Y is chlorine, bromine or iodine, either in the form of one of the salts e.g. an alkaline salt, or in the free form in the presence of an acid binding agent such as an alkali carbonate, bicarbonate, tertiary amine or the like or, so long as no undesired side reactions arise, even in the presence of an alcoholate, to react with a compound of the formula

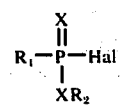

wherein $R_1$, $R_2$ and X have the meanings given for formula I and Hal is chlorine or bromine atom.

b. In the case where $R_1$ is a $C_1 - C_4$ alkoxy-, an amino-, a $C_1 - C_4$ alkylamino- or a bis-($C_1 - C_4$ alkyl)amino group, while $R_2$ is $C_1 - C_4$ alkyl, compounds of the general formula

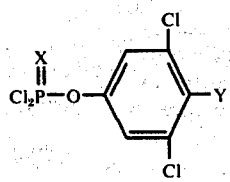

wherein X and Y have the meaning given for formula I, may be reacted in optional sequence with an alkali alcoholate, amine or ammonia corresponding to $R_1$ and an alkali alcoholate corresponding to $R_2$.

Reactions a) and b) are preferably carried out in inert solvent media and at a reaction temperature between 0° and 150° C.

The following are suitable as inert solvents or diluents, e.g. ether and ether type compounds such as diethylether, dipropylether, dioxane, tetrahydrofurane; amides such as N,N-dialkylated carboxylic acid amides; aliphatic, aromatic and halogenated hydrocarbons, particularly benzene, toluene, xylenes, chloroform and chlorobenzene; nitriles such as acetonitrile and dimethylsulfoxide.

Starting materials of formulae III and IV are partly known and can be manufactured by methods known per se.

The active substances of formula I are suitable for combating the most varied animal and vegetable pests.

Above all, they are effective against all stages of development such as e.g. eggs, larvae and pupae of insects and representatives of the order Acarina such as mites and ticks.

The compounds of formula I can, for example, be used against the following insects or representatives of the order Acarina:

Insects of families:
Teltigonidae
Gryllidae
Gryllotalpidae
Blattidae
Peduviidae
Phyrrhocoriae
Cimicidae
Delphacidae
Aphididae
Diaspididae
Pseudococcidae
Scarabaeidae
Dermestidae
Coccinellidae
Tenebrionidae
Chrysomelidae
Bruchidae
Tineidae
Noctindae
Lymatriidae
Pyralidae
Culicidae
Tipulidae
Stomoxydae
Trypetidae
Muscidae
Calliphoridae and
Pulicidae,
as well as Acarina of the families:
Ixodidae
Argasidae
Tetranychidae and
Dermanyssidae The insecticidal or acaricidal action can be substantially broadened and matched to given circumstances by the addition of other insecticides and/or acaricides.

As additives there are, for example, the following substances:
Bis-O,O-diethylphosphoric acid anhydride (TEPP)
Dimethyl (2,2,2-trichlor-1-hydroxyethyl) phosphonate (TRICHLORFON)
1,2-dibrom-2,2-dichloroethyldimethylphosphate (NALED)
2,2-dichlorvinyldimethylphosphate (DICHLORVOS)
2-methoxycarbamyl-1-methylvinyldimethylphosphate (MEVINPHOS)
Dimethyl-1-methyl-2-(methylcarbamoyl) vinylphosphate cis (MONOCROTOPHOS)
3-(dimethoxyphosphinyloxy-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-ethylthio)ethyldithiophosphate (DISULFOTON)
O,O-dimethyl-S-2-(ethylsulphinyl)ethylthiophosphate (OXYDEMETONMETHYL)
O,O-dimethy-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nnitrophenylphenylthiophosphate (EPN)
O,O-dimethyl-O-(4-nitro-m-tolyl)thiophosphate (FENITROTHION)
O,O-dimethyl-O-2,4-5-trichlorphenylthiophosphate (FENCHLORPHOS)
O-ethyl-O,2,4,5-trichlorphenylethylthiosphosphate (TRICHLORONATE)
O,O-dimethyl-O-2,5-dichlor-4-bromphenylthiophosphate (BROMOPHOS)
O,O-dimethyl-O-(2,5-dichlor-4-jodphenyl)-thiophosphate (JODOFENPHOS)
4-tert. butyl-2-chlorphenyl-N-methyl-O-methylamidophosphate (CRUFOMATE)
O,O-dimethyl-O-(3-methyl-4-methylmercaptophenyl)-thiophosphate (FENTHION)
Isopropylamino-O-ethyl-O-(4-methylmercapto-3-methylphenyl)phosphate
O,O-diethyl-O-p-(methylsulphinyl)phenyl-thiophosphate (FENSULFOTHION)
O-p-(dimethylsulfamido)phenyl O,O-dimethylthiophosphate (FAMPHUR)
O,O,O',O'-tetramethyl-O-O'-thiodi-p-phenylenthiophosphate
O-ethyl-S-phenyl-ethyldithiophosphate
O,O-dimethyl-O-(α-methylbenzyl-3-hydroxycrotony)-phosphate
2-chlor-1-(2,4-dichlorphenyl)vinyl-diethylphosphate (CHLORFENVINPHOS)
2-chlor-1-(2,4,5-trichlorphenyl)vinyl-dimethylphosphate
O-[2-chlor-1-(2,5-dichlorphenyl)]-O,O-diethylthiophosphate Phenylglyoxylonitriloxim-O,O-diethylthiophosphate (PHOXIM)
O,O-diethyl-O-(3-chlor-4-methyl-2-oxo-2-H-1-benzopyran-7-yl)thiophosphate (COUMAPHOS)
2,3-p-dioxandithiol-S,S-bis(O,O-diethyldithiophosphate (DIOXATHION)
5-[(6-chlor-2-oxo-3-benzoxazolinyl)methyl]O,O-diethyldithiophosphate (PHOSALONE)
2-(diethoxyphosphinylimino)-1,3-dithiolane
O,O-dimethyl-S-[2-methoxy-1,3,4-thiadiazol-5-(4H)-onyl-(4)methyl]dithiophosphate
O,O-dimethyl-S-phthalimidomethyl-dithiophosphate (IMIDAN)
O,O-diethyl-O-(3,5,6-trichlor-2-pyridyl)thiophosphate
O,O-diethyl-O-2-pyrazinylthiophosphate (THIONAZIN)
O,O-diethyl-O-(2-isopropyl-4-methyl-6-pyrimidyl)thiophosphate (DIAZINON)
O,O-diethyl-O-(2-chinoxalyl)thiophosphate
O,O-dimethyl-S-(4-oxo-1,2,3-benzotriazin-3(4H)-ylmethyl)dithiophosphate (AZINPHOSMETHYL)
O,O-diethyl-S-(4-oxo-1,2,3-benzotriazin-3(4H)-ylmethyl)dithiophosphate (AZINPHOSETHYL)
S-[(4,6-diamino-s-triazin-2-yl)methyl]-O,O-dimethyldithiophosphate (MENAZON)
O,O-dimethyl-O-(3-chlor-4-nitrophenyl)thiophosphate (CHLORTHION)
O,O-dimethyl-O(or S)-2-(ethykthioethyl)thiophosphate (DEMETON-S-METHYL)
2-(O,O-dimethyl-phosphoryl-thiomethyl)-5-methoxypyron-4-3,4-dichlorbenzyl-triphenylphosphoniumchloride
O,O-diethyl-S-(2,5-dichlorphenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiophosphoryl)-3-thiavaleramide (VAMIDOTHION)
O,O-diethyl-O-[2-dimethylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichlor-4-bromphenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)
O,O-dimethyl-O-(2-chlor-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorphenylthiophosphate (DICHLORFENTHION)
O,2,4-dichlorphenyl-O-methylisopropylamidothiophosphate
O,O-diethyl-O-2,5-dichlor-4-bromphenylthiophosphate (BROMOPHOS-ETHYL)
Dimethyl-p-(methythio)phenylphosphate
O,O-dimethyl-O-p-sulfamidophenylthiophosphate
O-[p-(p-chlorpheny)azophenyl]O,O-dimethylthiophosphate (AZOTHOATE)
O-ethyl-S-4-chlorphenyl-ethyldithiophosphate
O-isobutyl-S-p-chlorphenyl-ethyldithiophosphate
O,O-dimethyl-S-p-chlorphenylthiophosphate
O,O-dimethyl-S-(p-chlorphenylthiomethyl)dithiophosphate
O,O-diethyl-p-chlorphenylmercaptomethyl-dithiophosphate (CARBOPHENOTHION)
O,O-diethyl-S-p-chlorphenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)Odithiophosphate
O,O-dimethyl-S-(carboisopropoxy-phenylmethyl)-dithiophosphate
O,O-diethyl-7-hydroxy-3,4-tetramethylene-coumarinyl-thiophosphate (COUMITHOATE) 2-methoxy-4-H-1,3,2-benzodioxaphosphorin-2-sulphide.
O,O-diethyl-O-(5-pjenyl-3-isooxazolyl)thiophosphate
2-(diethoxyphosphinylimino)-4-methyl-1,3-dithiolane
Tris-(2-methyl-1-aziridinyl)-phosphine oxide (METEPA)
S-(2-chlor-1-phthalimidoethyl)-O,O-diethyldithiophosphate
N-hydroxynaphthalimido-diethylphosphate
Dimethyl-3,5,6-trichlor-2-pyridylphosphate
O,O-dimethyl-O-(3,5,6-trichlor-2-pyridyl)thiophosphate
S-2-(ethylsulphonyl)ethyl dimethylthiolphosphate (DIOXYDEMETON-S-METHYL)
Diethyl-S-2-(ethylsulphinyl)ethyl dithiophosphate (OXYDISULFOTON)
Bis-O,O-diethylthiophosphoric acid anhydride (SULFOTEP)
Dimethyl-1,3-di(carbomethoxy)-1-propen-2-yl-phosphate
Dimethyl-(2,2,2-trichlor-1-butyroyloxyethyl)phosphate (BUTONATE)
O,O-dimethyl-O-(2,2-dichlor-1-methoxy-vinyl)phosphate
Bis-(dimethylamido)fluorphosphate (DIMEFOX)
3,4-dichlorbenzyl-triphenylphosphoniumchloride.
Dimethyl-N-methoxymethylcarbamoylmethyl-dithiophosphate (FORMOCARBAM)
O,O-diethyl-O-(2,2-dichlor-1-chlorethoxyvinyl)phosphate
O,O-dimethyl-O-(2,2-dichlor-1-chlorethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorphenylthiomethyl)dithiophosphate (METHYLCARBOPHENOTHION)
O,O-dimethyl-S-(ethylthiomethyl)dithiophosphate
Diisopropylaminofluorphosphate (MIPAFOX)
O,O-dimethyl-S-(morpholinylcarbamoylmethyl)dithiophosphate (MORPHOTHION)
Bismethylamido-phenylphosphate
O,O-dimethyl-S-(benzene sulphonyl)dithiophosphate
O,O-dimethyl-(S and O)-ethylsulphinylethylthiophosphate O,O-diethyl-O-4-nitrophenylphosphate
Triethoxy-isopropoxy-bis(thiophosphinyl)disulphide
2-methoxy-4H-1,3,2,benzodioxaphosphorin-2-oxide
Okta,ethylpyrophosphoramide (SCHRADAN)
Bis(dimethoxythiophosphinylsulphido)-phenylmethane
N,N,N',N'-tetramethyldiamidofluorphosphate (DIMEFOX)
O-phenyl-O-p-nitrophenyl-methanthiophosphonate (COLEP)
O-methyl-O-(2-chlor-4-tert. butyl-phenyl)-N-methylamidothiophosphate (NARLENE)
O-ethyl-O-2(2,4-dichlorphenyl)-phenylthiophosphonate
O,O-diethyl-O-(4-methylmercapto-3,5-dimethyphenyl)-thiophosphate
4,4'-bis-(O,O-dimethylthiophosphoryloxy)-diphenyldisulphide
O,O-di-(P-chlorethyl)-O-(3-chlor-4-methyl-cumarinyl-7)-phosphate
S-(1-phthalimidoethyl)-O,O-diethyldithiophosphate
O,O-dimethyl-O-(3-chlor-4-diethylsulphamylphenyl)-thiophosphate
O-methyl-O-(2-carbisopropoxyphenyl)-amidothiophosphate
5-(O,O-dimethylphosphoryl)-6-chlor-bicyclo(3.2.0)-heptadiene (1,5
O-methyl-O-(2i-propoxycarbonyl-1-methylvinyl)ethylamidothiophosphate Carbamic acid derivatives 1-naphthyl-N-methylcarbamate (CARBARYL)
2-butinyl-4-chlorophenylcarbamate
4-dimethylamino-3-tolyl-N-methylcarbamate (AMINOCARB)
4-methylthio-3,5-xylyl-N-methylcarbamate (METHIOCARB)
2-chlorophenyl-N-methylcarbamate (CPWC)
1-(dimethylcarbamoyl)-5-methyl-3-pyrazolyl-N,N-dimethylcarbamate (DIMETHILAN)
2,3-dihydro-2,2-dimethyl-7-benzofuranyl-N-methylcarbamate (CARBOFURAN)
2-methyl-2-methylthio-propionaldehyde-O-(methylcarbamoyl)-oxime (ALDICARB)
8-quinaldyl-N-methylcarbamate and its salts
3-isopropyl-5-methylphenyl-N-methylcarbamate (PROMECARB)
2-(1,3-dioxolan-2-yl)-phenyl-N-methylcarbamate (DIOXACARB)
2-(4,5-dimethyl-1,3-dioxolan-2-yl)phenyl-N-methylcarbamate
2-(1,3-dithiolan-2-yl)-phenyl-N-methylcarbamate
2-(1,3-dithiolan-2-yl)-phenyl-N,N-dimethylcarbamate
2-isopropoxyphenyl-N-methylcarbamate (ARPROCARB)
4-diallylamino-3,5-xylyl-N-methylcarbamate (ALLYXICARB)
1-isopropyl-3-methylpyrazol-5-yl-N,N-dimethylcarbamate (ISOLAN)
1-methylthio-ethylamino-N-methylcarbamate (METHOMYL)
2-(propargylethylamino)-phenyl-N-methylcarbamate
2-(propargylmethylamino)-phenyl-N-methylcarbamate
2-(dipropargylamino)-phenyl-N-methylcarbamate
3-methyl-4-(dipropargylamino)-phenyl-N-methylcarbamate
3,5-dimethyl-4-(dipropargylamino)-phenyl-N-methylcarbamate
2-(allyl-isopropylamino)-phenyl-N-methylcarbamate Nitrophenols & derivatives 4,6-dinitro,6-methylphenol, Na-salt (dinitrocresol)
dinitrobutylphenol(2,2',2'' triethanolamine salt)
2-cyclohexyl-4,6-dinitrophenol (dinex)
2-(1-methylheptyl)-4,6-dinitrophenyl-crotonate (dinocap)
2 sec.-butyl-4,6-dinitrophenyl-3-methyl-butenoate (binapacryl)
2 sec.-butyl-4,6-dinitrophenyl-cyclopropionate
2 sec.-butyl-4,6-dinitrophenyl-isopropyl carbonate (dinobuton)

Various pyrethrin I
pyrethrin II
3-allyl-2-methyl-4-oxo-2-cyclopentene-1-yl-chrysanthemumat (allethrin)
6-chloropiperonyl-chrysanthemumate (barthrin)
2,4-dimethylbenzyl-chrysanthemumate (dimethrin)
2,3,4,5-tetrahydrophthalimidomethylchrysanthemumate
4-chlorobenzyl-4-chlorophenylsulfide (chlorbenside)
6-methyl-2-oxo-1,3-dithiolo-(4,5-b)-quinoxaline (quinomethionate)
(1)-3-(2-furfuryl)-2-methyl-4-oxocyclopent-2-onyl
(1)-(cis + trans) chrysanthemum-monocarboxylate (furethrin)
2-pivaloyl-indan-1,3-dione (pindone)
N'-(4-chloro-2-methylphenyl)-N,N-dimethylformamidine (chlorphenamidine)
4-chlorobenzyl-4-fluorphenyl-sulfide (fluorbenside)
5,6-dichlor-2-phenoxycarbanyl-2-trifluormethyl-benzimidazole (fenazaflor)
p-chlorophenyl-p-chlorobenzenesulfonate (chlorfenson)
p-chlorphenyl-benzene sulfonate (fenson)
p-chlorphenyl-2,4,5-trichlorphenylsulfone (tetradifon)
p-chlorphenyl-2,4,5-trichlorphenylsulfide (tetrasul)
p-chlorbenzyl-p-chlorphenylsulfide (chlorbenside)
2-thio-1,3-dithiolo-(,5-6)quinoxaline (thioquinox)
prop-2-ynyl-(4-t-butylphenoxy)-cyclohexylsulfite (propargil)

Additionally the new compounds of formula I have exceptionally good nematocidal properties and can be used, for example, for combating the following plant parasitic nematodes: *Meloidogyne spp.*, *Heterodera spp.*, *Ditylenchus spp.*, *Pratylenchus spp.*, *Paratylenchus spp.*, *Anguina spp.*, *Helicotylenchus spp.*, *Tylenchorhynchus spp.*, *Rotylenchulus spp.*, *Tylenchulus semipenetrans*, *Radopholus similus*, *Belonolaismus spp.*, *Trichodorus spp.*, *Longidorus- spp.*, *Aphelenchoides spp.*, *Xiphinema spp.*

The compounds of formula I have, apart from the properties noted above, in very small application doses satisfactory effectiveness against representatives of the class Thallophyta.

Some of these compounds also show bactericidal action. However they are, above all, effective against fungi, particularly against the following classes, orders and types of phytopathogeneic fungi.

Oomycetes such as Plasmodiophora types, Aphanomyces types, Pythium types, Phytophthora types, e.g. (Phytophthora infestans, Phytophthora cactorum), Plasmopara types, e.g. (Plasmopara viticola).

Bremia types (Bremia lactucae), Peronospora types, e.g. (Peronospora tabacina). Pseudoperonospora types, e.g. (Pseudoperonospora humuli).

Zygomycetes such as Rhizopus types.

Ascomycetes such as Eurotiales, such as Aspergillus types, Penicillium types, e.g. (*Penicillium digitatum, Penicillium italicum*), Taphrinales, such as Taphrina types, e.g. (*Taphrina deformans*), Erysiphales, such as Erysiphes types, e.g. (*Erysiphes cichoracearum, Erysiphes graminis*), Podosphaera leucotricha, Sphaerotheca types (*Sphaerotheca pannosa*), Uncinula types (*Uncinula necator*), Helotiales, such as Monilina types (Monilinia [Sclerotinia] fructicola, Monilinia laxa), Diplocarpon types (*Diplocarpon rosae*), Pseudopeziza types, Sphaeriales, such as Nectria types (*Nectria galligena*), Ceratocystis types, Pseudosphaeriales, such as Ventura types (*Venturia inaequalis*), Mycosphaerella types, Ophiobolus types (*Ophiobolus graminis*), Cochliobolus types (Helminthosporium) miyabeanus), Cercospora types, (*Cercospora beticola, Cercospora musae*).

Basidiomycetes, such as Aphyllophorales, Pellicularia types, e.g.

(*Pellicularia filamentora* = (*Rhizoctonia solani*) ), Uredinales, such as Puccinia types, e.g. (*Puccinia triticina*), Uromyces types (*Uromyces phaseoli*), Hemileia types, (*Hemileia vastatrix*), Cronartium types (*Cronartium ribicola*), Phragmidium types (*Phragmidium subcorticium*), Gymnosporangium types.

Denteromycetes = (Fungi imperfecti)

such as Piricularia types, e.g. (*Piricularia oryzae*), Corynespora types. Thielaviopsis types, Clasterosporium types, Botrytis types (*Botrytis cinerea*), Cladosporium types, Alternaria types, (*Alternaria solani*), Verticillium types (*Verticillium albo-atrum*), Phialophora types, Melanconiales, such as Colletotrichum types, Fusarium types such as (*Fusarium oxysporum, Fusarium nivale*), Gloesporium types (*Gloeosporium fructigenum*), Sphaeropsidales, e.g. Septoria types (*Septoria apicola*), Diplodia types, (*Diplodia natalensis*), Mycelia sterilia, e.g. Sclerotium types (*Sclerotium rolfsii*). The compounds of formula I likewise show a fungitoxic action on moulds which attack the plants from the soil and partly cause tracheomycosos such as e.g. Fusarium cubense, Fusarium dianthi, Verticillium alboatrum and Phialophora cinereceus.

Furthermore the new substances can be used for the treatment of seeds, fruits, buds, etc., for protecting them from mould infections for example from blights of all types, such as:

Ustilaginales, such as Ustilago types (Ustilago avenae)
Tilletia types (Tilletia tritici),
Urocystis and Tuburcinia types
Phoma types (Phoma betae).

On account of their biocidal properties the compounds of formula I are suitable for disinfecting and for protecting most varied materials from attack by bacteria and moulds. In this connection it is especially advantageous that the compounds of formula I have no toxic symptoms or side effect against warmblooded animals at the concentrations at which they are necessary for disinfection and materials protection.

The compounds of Formula I can be formulated not only with the insecticides and acaricides mentioned, but also with other fungicides, fungistatic agents or bacteriostatic agents in varying mixture proportions, by means of which mixtures of compounds may be produced which have advantages compared with their individual components. For formulating with the substances of formula I there are suitable, for example:

dodecylguanidine acetate (DODINE)
pentachloronitrobenzene (QUINTOZENE)
pentachlorophenol (PCP)
2-(1-methyl-n-propyl)-4,6-dinitrophenyl-2-methylcrotonate (BINAPACRYL)
2-(1-methyl-n-heptyl)-4,6-dinitrophenylcrotonate (DINOCAP)
2,6-dichlor-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichlormethylthio) phthalimide (FOLPAT)
N-(trichloromethylthio)cyclohex-4-en-1,2-dicarboximide (CAPTAN)
N-(1,1,2,2-tetrachloroethylthio)cyclohex-4-en-1,2-dicarboximide (CAPTAFOL)
N-methansulfonal-N-trichlormethylthio-chloroaniline
N'-dichlorofluoromethylthio-N,N-dimethyl-N'-phenyl-sulfamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric) (MANEB)
tetramethylthiuramdisulfide (THIRAM)
1-oxy-3-acetyl-6-methyl-cyclohexene-(5)dione-(2,4) (DEHYDROACETIC ACID)
8-hydroxyquinoline (8-QUINOLINOL)
2-dimethylamino-6-methyl-5-n-butyl-4-hydroxy-pyrimidine
methyl-N-benzimidazol-2-yl-N-(butylcarbamoyl)carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine pentachlorobenzyl alcohol.

The compounds of formula I can be used alone or together with suitable carriers and/or additive materials. Suitable carriers and additives can be solid or liquid and correspond to the materials normally used in the formulation art such as, e.g. natural or regenerated materials, solvents, dispersing agents, wetting agents, adhesives, thickening agents, binders and/or fertilizers.

For application the compounds of formula I can be made up to dusting agents, emulsion concentrates, granulates, dispersions, sprays, solutions or suspensions in a customary formulation technique which are known generally in the application art. Cattle dips and spray races in which aqueous preparations are used should be particularly noted.

The manufacture of materials according to the invention takes place in fashion known per se by intimate mixing and/or milling of active substances of formula I with suitable carrier materials, optionally with the addition of dispersing agents or solvents inert to the active substances. The active substances can be present in the following use forms and can be used therein:

Solid use forms:
dusting agents, spreading agents, granulates, coated granulates, impregnated granulates, and homogeneous granulates, Liquid use forms:

a. active substance concentrates dispersable in water wettable powders, pastes, emulsions;

b. solutions

For the manufacture of solid use forms (dusting agents, spreading agents) the active substances are mixed with solid carrier materials. As carrier materials there are for example kaolin, talcum, bolus, loess, chalk, limestone, limestone grit, attaclay, dolomite, diatomaceous earth, precipitated silica, alkaline earth metal silicates, sodium and potassium aluminium silicates (feldspars and mica) calcium and magnesium sulphate, magnesium oxide, ground plastics materials, fertiliers such as ammonium sulphate, ammonium phosphate, ammonium nitrate, urea, ground vegetable products such as crop flour, bark flour, wood flour, nutshell flour, cellulose powder, residues from plant extraction, active carbon etc. Each used as such or used as mixtures with one another.

The particle size of the carrier material amounts for dusting agents suitably to about 0.1 mm, for spreading agents about 0.075 to 0.2mm or more.

To these mixtures there can furthermore be added additives stabilising the active substance and/or non-ionic, anion active and cation active materials which, for example, improve the adherence of the active substances to the plants and plant parts (adhesives and glues) and/or guarantee a better wetting (wetting agents) or dispersability (dispersing agents).

For example, the following materials may be used: olein-lime-mixtures, cellulose derivatives (methyl cellulose, carboxymethyl cellulose) hydroxyethylene glycol ethers of mono- and dialkyl phenols with 5–15 ethylene oxide groups per molecule and 8–9 carbon atoms in the alkyl group, ligninsulfonic acids, their alkaline and alkaline earth salts, polyethylene glycol ethers (carbowaxes) fatty alcohol polyglycol ethers with 5–20 ethylene oxide groups per molecule and 8–18 carbon atoms in the fatty alcohol part, condensation products of ethylene oxide, propylene oxide, polyvinyl pyrrolidone, polyvinyl alcohol, condensation products of urea formaldehyde as well as latex products.

Active substance concentrates dispersable in water, i.e. wettable powders, pastes and emulsion concentrates, are materials which can be diluted with water to any desired concentration. They consist of active substance, carrier, optionally additives stabilising the active substance, surface active materials and anti-foaming agents and if desired solvents.

The wettable powders and pastes are obtained by mixing and milling the active substance with dispersing agents and powder carrier materials in suitable apparatus until homogeneity. As carrier materials there can be used, for example, those noted above for the solid use forms. In some cases it is advantageous to use mixtures of various carrier materials. As dispersing agents there can be used for example: condensation products of sulfonated naphthalene and sulfonated naphthalene derivatives with formaldehyde, condensation products of naphthalene or naphthalene sulfonic acid with phenol and formaldehyde as well as alkali, ammonium, alkaline earth salts of ligninsulfonic acid. Furthermore, alkyl aryl sulfonates, alkaline and alkaline earth metal salts of dibutyl naphthalene sulfonic acid, fatty alcohol sulphates, such as salts of sulphated hexadecanols, heptadecanols, octadecanols and salts of sulphated fatty acid glycol ethers, the sodium salt of oleyl methyl-tauride, ditertiary acetylene glycols, dialkyldilaurylammonium chloride and fatty acid alkaline and alkaline earth metal salts.

Silicones can be used as anti-foaming agents.

The active substances are so mixed, milled, sieved and graded with the above noted additives, that for sprayable powders the solid portion has a particle size of 0.02 to 0.04mm and for pastes does not exceed 0.03mm. For the manufacture of emulsion concentrates and pastes, dispersing agents such as are noted in the previous sections are used, together with organic solvents and water. The solvents there are, for example, alcohols, benzene, xylenes, toluene, dimethylsulfoxide, and mineral oil fractions boiling in the range of 120°–350° C.

The solvents must be practically odorless, non-phytotoxic and inert with respect to the active substances.

Furthermore, the materials according to the invention can be used in the form of solutions. For this, one or more active substances of general formula I is dissolved in suitable organic solvents, solvent mixtures or water. As organic solvents there can be used aliphatic and aromatic hydrocarbons, their chlorinated derivatives, alkyl naphthalenes, mineral oils alone or in admixture with one another.

The content of active substance in the materials described above lies between 0.1 and 95% and in this connection it should be noted that in application from aircraft or by means of other suitable application devices, concentrations of up to 99.5% or even pure active substance can be used.

The active substances of formula I can be formulated for example as follows:

Dusting Agent: For the manufacture of an (a) 5% and (b) 2% dusting agent, the following materials are used:
  a. 5 parts active substance
     95 parts talcum
  b. 2 parts active substance
     1 part highly dispersed silicic acid
     97 parts talcum The active substances were mixed and milled with the carrier materials.

Granulate: For the manufacture of a 5% granulate, the following materials were used:
  5 parts active substance
  0.25 parts epichlorohydrin
  0.25 parts cetylpolyglycol ether
  3.50 parts polyethylene glycol
  91 parts kaolin (particle size 0.3–0.8mm).

The active substance was mixed with epichlorohydrin and dissolved in 6 parts acetone. Thereafter polyethyleneglycol and cetylpolyglycol ether were added thereto. The so obtained solution was sprayed onto kaolin and then the acetone was evaporated in vacuo.

Wettable powder: for the manufacture of an (a) 40% (b) and (c) 25% and (d) 10% sprayable powder the following components were used:
  a. 40 parts active substance
     5 parts ligninsulfonic acid sodium salt
     1 part dibutylnaphthaline sulfonic acid sodium salt
     54 parts silicic acid
  b. 25 parts active substance
     4.5 parts calcium lignosulfonate
     1.9 parts champagne-chalk hydroxyethylcellulose mix (1:1)
     1.5 parts sodium dibutylnaphthalene sulfonate
     19.5 parts silicic acid
     19.5 parts champagne-chalk 28.1 parts kaolin
c. 25 parts active substance
  2.5 parts icooctylphenoxy polyoxyethylene ethanol
  1.7 parts champagne-chalk hydroxyethylcellulose mixture (1:1)
  8.3 parts sodium aluminium silicate
  16.5 parts kieselguhr
  46 parts kaolin;
d. 10 parts active substance
  3 parts of a mixture of sodium salts of saturated fatty alcohol sulphates,
  5 parts naphthalene sulfonic acid formaldehyde condensate
  82 parts kaolin.

The active substances were intimately admixed in suitable mixers with the additives and milled on suitable mills and rolls. Wettable powders were obtained which could be diluted with water to give suspensions of any desired concentration.

Emulsifiable concentrates: For the manufacture of an (a) 10% and (b) 25% emulsifiable concentrate the following materials were used:
a. 10 parts active substance
  3.4 parts epoxidised vegetable oil
  13.4 parts of a combination emulsifier consisting of fatty alcohol polyglycol ether and alkylarylsulfonate calcium salt
  40 parts dimethylformamide
  43.2 parts xylene
b. 25 parts active substance
  2.5 parts epoxidised vegetable oil
  10 parts of an alkylarylsulfonyl fatty alcohol polyglycol ether mixture
  5 parts dimethylformamide
  57.5 parts xylene;
  By dilution with water emulsions of any desired concentration can be made from these concentrates.

Spraying agents: For the manufacture of a 5% spraying agent, the following components were used:
  5 parts active substance
  1 part epichlorohydrin
  94 parts petrol (boiling range 160°–190° C);

The following examples will serve to illustrate the invention.

EXAMPLE 1

Manufacture of O,O-dimethyl-O-(3,4,5-trichlorophenyl)-thiophosphate 29.6g 3,4,5-trichlorophenol were dissolved in 250 ml methylethyl ketone. 25.0g anhydrous $K_2CO_3$ were added thereto and the mixture stirred for 1 hour at room temperature. Thereafter within about a quarter of an hour 26.0g dimethylchlorothiophosphate were dropped into the reaction mixture. The mixture was then stirred for 1 hour at room temperature and then for 5 hours at 70° C. After cooling the reaction mixture was poured into 500ml water, the product extracted with 200ml benzene, washed with water and dried. After distilling off the solvent, 46.2g of an almost colourless product were obtained.

Analysis for $C_8H_8Cl_3O_3PS$:

| Analysis for $C_8H_8Cl_3O_3PS$: | | |
|---|---|---|
| | calculated | found |
| For P | 9.6% | 9.2% |
| For Cl | 33.1% | 33.0% |
| Boiling point: 120° C/0.002 Torr. | | |

EXAMPLE 2

The manufacture of methylamido-O-ethyl-O-(3,4,5-trichlorophenyl)-thionophosphonate.

49.6g 3,4,5-trichlorophenylthiophosphoric acid chloride were dissolved in 150 ml tetrahydrofurane. With stirring and cooling a sodium ethylate solution of about 3.45g Na in 100 ml absolute ethanol were added thereto dropwise. The reaction mixture was then stirred for a further half-an-hour. Then a solution of 9.34g methylamine in 60ml tetrahydrofuran was added dropwise into the reaction mixture at 0°–10° C. The reaction mixture was then further stirred for 8 hours at room temperature poured into water and extracted with benzene. The benzene phase was washed with 3% $Na_2CO_3$ solution and water, dried with sodium sulphate and freed from solvent by distilling off. 45.6g of a light-yellow oil were obtained.

Analysis for $C_9H_{11}Cl_3NO_2PS$:

| Analysis for $C_9H_{11}Cl_3NO_2PS$: | | |
|---|---|---|
| | calculated | found |
| For P | 9.3% | 9.2% |
| For Cl | 31.8% | 33.0% |

Analogously to examples 1 and 2, the following compounds were also manufactured:

| Analogously to examples 1 and 2, the following compounds were also manufactured: | |
|---|---|
| Formula: | Physical data: |
| 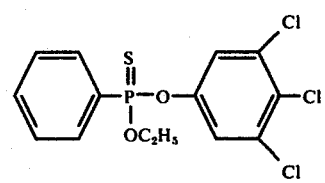 | B.Pt. 140° C/0,001 Torr |

-continued
Analogously to examples 1 and 2, the following compounds were also manufactured:
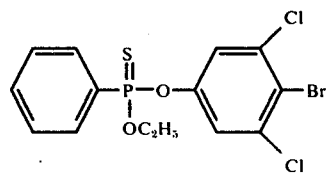 B.Pt. 150° C/0.001 Torr
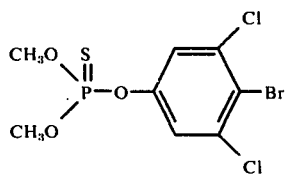 B.Pt. 130° C/0.001 Torr
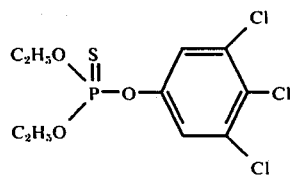 B.Pt. 130° C/0.03 Torr
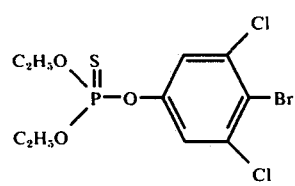 B.Pt. 130° C/0.001 Torr
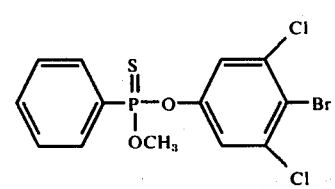 B.Pt. 145° C/0.001 Torr
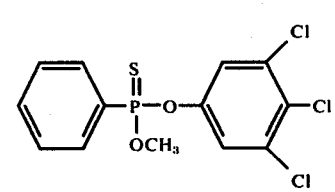 M.Pt. 55° C
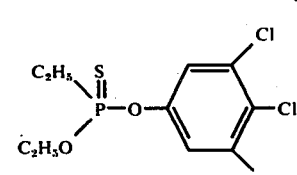 B.Pt. 128° C/0.02 Torr
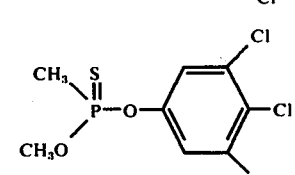 B.Pt. 113° C/0.001 Torr
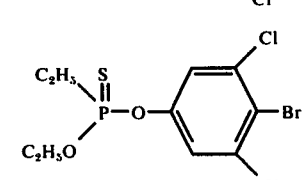 B.Pt. 142° C/0.11 Torr -continued
Analogously to examples 1 and 2, the following compounds were also manufactured:
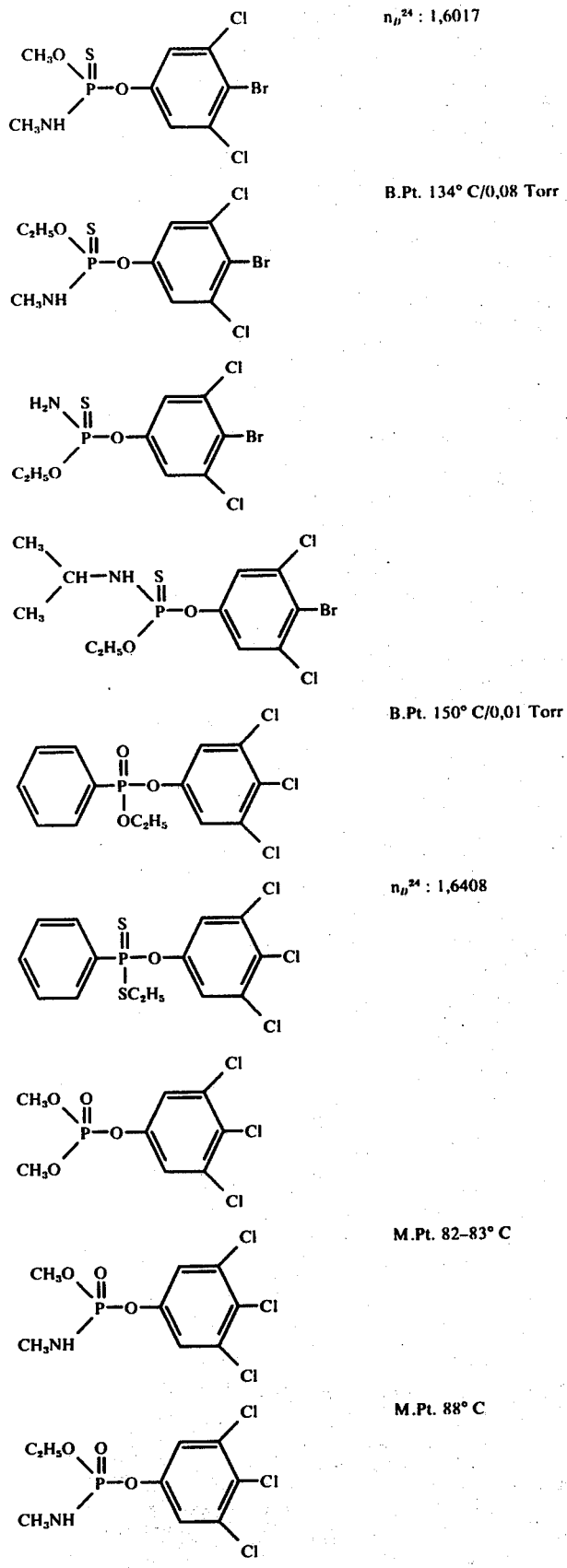
$n_D^{24}: 1,6017$
B.Pt. 134° C/0,08 Torr
B.Pt. 150° C/0,01 Torr
$n_D^{24}: 1,6408$
M.Pt. 82–83° C
M.Pt. 88° C -continued Analogously to examples 1 and 2, the following compounds were also manufactured:

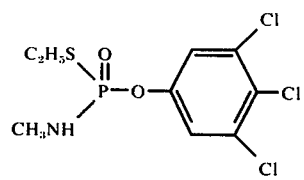

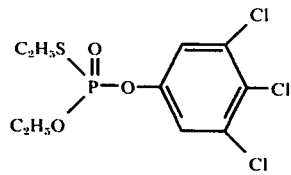

$n_D^{24}$ : 1,5545

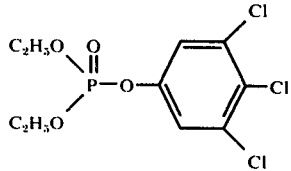

B.Pt. 127° C/0,06 Torr

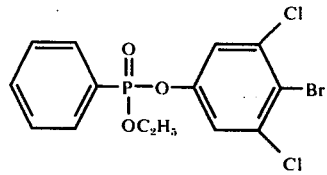

B.Pt. 150° C/0,001 Torr
(Mol. Dest.)

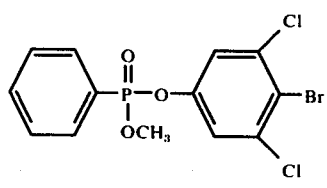

B.Pt. 145° C/0,001 Torr
(Mol. Dest.)

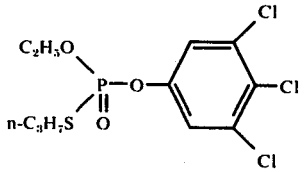

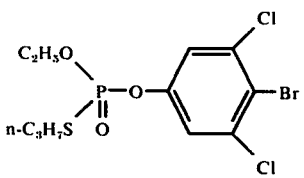

EXAMPLE 3

Insecticidal ingestion-effect

Cotton plants and potato bushes were sprayed with a 0.05% aqueous emulsion of active substance (obtained from a 10% emulsifiable concentrate).

After drying the substrate, the cotton plants were infected with Disdercus fasciatus nymphs and the potato bushes with colorado beetle larvae (Leptinotarsa decemlineata). The test was carried out at 24° C and 60% relative humidity.

The compounds according to examples 1–3 show in the above test a good insecticidal ingestion action against Disdercus fasciatus and Leptinotarsa decemlineata.

EXAMPLE 4

Systemic insecticidal action

For determining the systemic action, rooted bean plants (Vicia fabae) were set in a 0.01% aqueous solution of aqueous substance (obtained from 10% emulsifiable concentrate). After 24 hours black bean aphid (Aphis fabae) were set on the parts of the plant above the earth. By means of a special device, the animals were protected from contact and gas action. Test was carried out at 24° C and 70% relative humidity.

In the above test the compounds according to examples 1–3 show a good systemic insecticidal action against Aphis fabae.

EXAMPLE 5

Acaricidal action a. Action on mites (Tetranychus urticae)

For testing the acaricidal action bean leaves, which were attacked by adults, intermediate stages and eggs of the red spider mite (Tetranychus urticae) were treated with 0.05% aqueous emulsion of the substance to be tested (manufactured from a 25% emulsifiable concentrate). After 6 days the test was evaluated. As test animals a strain of red spider mites resistant to phosphoric acid esters was used.

b. Action on ticks (Boophilus microplus) and their development stages

For the following test 10 adults were used in each case which were ready to lay. The adult ticks were dipped for 3 minutes in an aqueous emulsion of active substance (concentration see column below).

The ticks were then kept at 27° C and 80% relative humidity. At 5, 10 and 15 days the egg lay was determined.

The compounds according to examples 1 and 3 which were tested by the above tests (a) and (b) show the good action against Tetranychus urticae and *Boophilus microplus*.

EXAMPLE 6

Fungicidal action a. Action against Botrytis cinerea on Vicia faba

In petri dishes which had been lined with moistened filter paper, 3 fully developed equal sized leaves of Vicia faba were laid per dish, with the leaves having been sprayed dripping wet by a spraying apparatus with a spray made from a 10% sprayable powder formulation containing the active substance (0.1% active substance content). When the leaves were dry again, they were infected with a standardized spore suspension of the mould (concentration 100,000 spores/ml) and kept for 48 hours in a damp atmosphere at 20° C. After this time there showed up black at first point shaped flecks, which rapidly broadened. The number and size of the infection points served as an evaluation measure for the effectiveness of the substance under test.

b. Action against Erysiphe cichoracearus on Cucumis sativus

Young Cucumis sativus plants were sprayed with a spore suspension of the mould after they had been sprayed with a 0.1% suspension of the active substance formulated as a sprayable powder and after drying of the sprayed layer. After 8 days in a greenhouse at about 23° C the degree of attack (proportion of the leaf surface coated with Kycelia) was determined on the infected treated leaves in comparison to untreated infected controls.

c. Action against Uromyces appendienlatus on Phaseolus vulgaris

Phaseolus vulgaris plants in the two-leaf stage were sprayed dripping wet with a suspension of active substance made from a wettable powder (concentration 0.1% active substance). After drying the sprayed layer, the plants were infected with a fresh spore suspension of bean rust and then kept for one day in a damp chamber and then 12 days in a greenhouse at 20°–22° C.

The size and number of the rust pustules served as a standard of evaluation for the effectiveness of the substance under test.

d. Action against Phytophthora infestans on Solanum Lycopersicum

S.Lycopersicum-plants of the same type and the same stage of development were kept in dry condition after spraying with a spray of 0.1% active substance (manufactured from a wettable powder containing an active substance) and they were then sprayed with a Zoospore suspension of Ph.infestans until they were dripping wet. They then remained for 6 days in a greenhouse at 18°–20° C and high relative humidity (95–100%) and showed after this time typical leaf-flecks. On the basis of their number and size the evaluation of the substance under test was carried out.

e. Action against Podosphaera leucotricha (Ell. et Ev.) Salm. on apple saplings

Apple shoots of type MN 111 were grown in the greenhouse for a period of the test at 20° C and 90% relative humidity. When 3 or 4 leaves on the growing side shoots had unfolded, the leaves were sprayed dripping wet with a spray (active substance content 0.1%) made from a active substance formulated as 10% wettable powder. After drying the sprayed layer, the leaves were sprayed regularly on the upper side with a spore suspension of the mould.

7 and 14 days after the first treatment, the saplings were again sprayed with the above described preparation of active substance. 12 days after the last treatment, the evaluation of the test took place.

Size and number of the infection points served as an evaluation measured for the effectiveness of the substance under test.

f. Action against Plasmopara viticola (Bert. et Curt.) (Berl. et DeToni) on vines In a greenhouse vine saplings of type "Chasselas" were cultured. In the 10-leaf stage three plants were sprayed dripping wet with a spray (active substance content 0.1%) of active substance which had been formulated up as a 10% sprayable powder. After drying on of the sprayed layer the plants were evenly infected on the undersides of the leaves with the spore suspension of the mould. The plants were then kept for 8 days in a damp chamber by the control plants. Number and size of the infection posititons served as an evaluation measure for the effectiveness of the test substance.

g. Action against Septoria apicola Spegazzini on Celery plants

In a greenhouse celery of types "Challon" was cultured. 15cm high plants were sprayed with a spray (active substance content 0.1%) until they were dripping wet, the spray having been made from an active substance formulated out as a 10% wettable powder. After drying of the sprayed layer they were infected with a spore suspension of the mould. After 2 days in the damp chamber and 12 days at 20°–22° C and 90% relative humidity in the greenhouse disease symptoms arose. The number and size of the infection sites served as an evaluation measure for the effectiveness of the substance under test.

h. Action against Erysiphe graminis DC. on Triticum

In a greenhouse at 20° C young wheat plants of about 10cm length were sprayed dripping wet with a spray (active substance content 0.1%) which had been made from an active substance formulate up as a 10% wettable powder. After drying the sprayed layer, the plants were infected with exospores of the mould. After 12 days (greenhouse 20° C) the percentage attack of the plant was determined.

i. Action against Puccinia triticina Eritess on Triticum

In a greenhouse at 20° C young wheat plants of about 10cm length were sprayed dripping wet with a spray (active substance content 0.1%) made from an active substance formulated up as a 10% wettable powder. After drying on of the sprayed layer the plants were infected with a ureidospore suspension of the mould evenly. After 5 days in the damp chamber and 12 days in the greenhouse at 20°–22° C and normal relative humidity evaluation took place. The number and size of the infection sites served as an evaluation measure for the effectiveness of the test substance.

Compounds according to examples 1–3 showed good fungicidal action in the above tests (a) to (i).

EXAMPLE 7

Action against soil nematodes

For testing the action against soil nematodes the active substance was given in the concentration noted and intimately mixed into earth which was infected by root knot nematodes (Meloidogyne avenaria). Into the so prepared earth in test row A tomato seedlings were planted directly thereafter and in test row B tomatoes were sown after 8 days delay.

For testing the nematocidal action 28 days after planting or sowing the number of galls on the roots were counted.

In this test the active substances according to examples 1–3 showed good action against Meloidogyne Avenaria.

I claim:

1. An insecticidal and acaricidal composition comprising an insecticidally and acaricidally effective amount of a compound of the formula 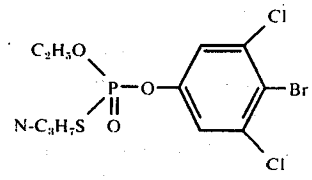 together with a suitable inert carrier therefor.

2. An insecticidal and acaricidal composition comprising an insecticidally and acaricidally effective amount of the compound of the formula 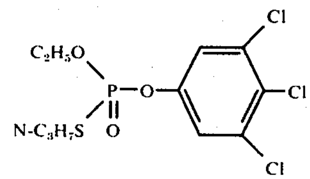 together with a suitable inert carrier therefor.

3. A method for combatting insects and acarids which comprises applying to the loci thereof an insecticidally and acaricidally effective amount of the compound of claim 1.

4. A method for combatting insects and acarids which comprises applying to the loci thereof an insecticidally and acaricidally effective amount of the compound of claim 2.

* * * * *